United States Patent [19]

Yasunaga

[11] Patent Number: 5,517,182

[45] Date of Patent: May 14, 1996

[54] METHOD FOR CO DETECTION AND ITS APPARATUS

[75] Inventor: Susumu Yasunaga, Osaka, Japan

[73] Assignee: Figaro Engineering Inc., Osaka, Japan

[21] Appl. No.: 309,163

[22] Filed: Sep. 20, 1994

[51] Int. Cl.[6] .................................................. G08B 17/10
[52] U.S. Cl. .......................... 340/634; 340/632; 422/94; 422/98; 338/34; 73/31.05; 73/31.06
[58] Field of Search ..................................... 340/634, 632; 422/90, 94, 95, 98; 338/34, 35; 73/31.05, 31.06

[56] References Cited

U.S. PATENT DOCUMENTS

| | | | |
|---|---|---|---|
| 3,750,123 | 7/1973 | Caillouet, Jr. | 340/634 |
| 3,906,473 | 9/1975 | Le Vine | 340/634 |
| 4,443,791 | 4/1984 | Risgin | 340/634 |
| 4,535,315 | 8/1985 | Sakai | 338/34 |
| 4,567,475 | 1/1986 | Bukowiecki et al. | 340/634 |
| 4,860,223 | 8/1989 | Grilk | 364/550 |
| 4,896,143 | 1/1990 | Dolnick et al. | 340/634 |

Primary Examiner—Brent A. Swarthout
Assistant Examiner—Julie B. Lieu
Attorney, Agent, or Firm—Nikaido, Marmelstein, Murray & Oram

[57] ABSTRACT

A CO detector, utilizing periodical temperature change of a metal oxide semi-conductor gas sensor, is equipped with a backup battery. When power cut of a commercial power supply is detected, the detector will be driven by the battery, and the gas sensor will be heated at 50°–100° C. for from 30 seconds to 1 minute and will be kept at room temperature for about 30 minutes. CO is detected by the minimum sensor output after the heating.

13 Claims, 15 Drawing Sheets

METHOD FOR CO DETECTION AND ITS APPARATUS

FIELD OF THE INVENTION

The present invention relates to detection of CO with metal oxide semi-conductor gas sensors and in particular to the backup of the detectors in case of power cut.

PRIOR ART

It was proposed by Mr. Le-Vine to heat a metal oxide semi-conductor gas sensor at a relatively high temperature and at a relatively low temperature alternately and repetitively for detecting CO by a sensor output at the lower temperature (U.S. Pat. No. 3,906,473), and the method has been widely used. Furthermore, U.S. Pat. Nos. 4,896,143 and 4,860,223 describe to accumulate the resultant CO detection signal statistically and to translate it into CO hemoglobin concentration in human blood.

Since CO detectors are safeguards, it is preferable to equip them with backup function in case of power cut at least for a night and preferably over 24 hours. However metal oxide semi-conductor gas sensors require too much power to back up them with a dry battery. For example, a CO sensor, TGS 203, which is commercially produced by the assignee, requires 70 mW for the lower temperature heating and 700 mW for the higher temperature heating. Since its operational cycle comprises 90 seconds for the lower temperature and 60 seconds for the higher temperature, its mean power consumption is as much as 320 mW. With the power consumption of the peripheral circuit added to this, the effective power consumption of a CO detector is about 400 mW, and a dry battery can support the detector only for about 2 hours. Therefore it is necessary to extremely reduce the power consumption of the gas sensor for the backup.

SUMMARY OF THE INVENTION

It is an object of the invention to reduce the power consumption of a gas sensor used in a CO detector for its backup, while maintaining the capability for CO detection.

It is a further object of the invention to provide a sampling method of CO concentration while reducing the power consumption.

It is a still further object of the invent ion to prevent false alarms by hydrogen, ethanol, or humidity in atmosphere, while reducing the power consumption.

It is a still further object of the invent ion to prevent alarms within an allowable concentration range of CO.

It is a still further object of the invention also to reduce the power consumption of the peripheral circuit.

The detector according to the invention usually heats a metal oxide semi-conductor gas sensor at a lower temperature and at a higher temperature alternately and detects CO by a sensor output at the lower temperature. When power cut or trouble of its power supply is detected, a backup battery will be switched on, and the gas sensor will be operated under a new heating cycle for reducing the power consumption. The new cycle comprises a short time pulsive heating period and a relatively long time non-heating period. The pulse heating period is, for example, from 5 seconds to 2 minutes, and preferably from 30 seconds to 90 seconds. The maximum temperature increase from ambient temperature during the pulse heating is, for example, between 30 and 150° C., preferably between 40 and 100° C., and most preferably between 40 and 80° C. The non-heating period is, for example, from 5 minutes to 2 hours, and preferably from 15 minutes to 45 minutes. Since the temperature of the gas sensor increases with time during the pulse heating, and furthermore the maximum temperature is not so high, the maximum temperature increase from ambient temperature is indicated. The power consumption of the gas sensor is inversely proportional to the non-heating period, proportional to the pulse heating period, and increases with the maximum temperature. The inventor has found the TGS 203 sensor is operable with power consumption of 1.8 mW under a condition that the difference between the maximum and ambient temperatures is from 40 to 50° C. with the pulse heating time of 45 seconds and the non-heating time of 30 minutes.

Under heating cycles for backup, a minimum sensor output, namely a maximum resistance of the metal oxide semi-conductor, appears after the pulse heating period. The minimum sensor output correlates strongly to the CO concentration. In air or in CO contaminated air, after the pulse heating, appears the minimum sensor output which correlates to CO concentration. In contrary to this, in H2 containing air, the sensor output decreases monotonically after the pulse heating without any clear minimum. Therefore a stationary sensor output after the pulse heating is to be sampled in place of the minimum sensor output, if no minima are sampled. Stationary sensor outputs in H2 containing air are too small for producing a false alarm, and the minimum sensor output in atmosphere containing less than 20 ppm CO, which affects little against human bodies and is within an allowable concentration, is also too small to generate a false alarm. Therefore, according to the invention, qualitative detection of CO which indicates the presence of CO above an allowable limit is performed. Furthermore the inventor has found the rain minimum sensor output is less affected by humidities in air than the other sensor output sampled at other timings.

When reducing the gas sensor power consumption enough, the peripheral circuit requires greater power than the gas sensor. For example, in reducing the gas sensor power consumption to about 2 mW, the power consumption of the peripheral circuit becomes more important, since a micro-computer for controlling the detector, an indicator LED, and an alarm buzzer require about 10 mW, respectively. It, therefore, is preferable to maintain the micro-computer ordinarily in a data hold mode, where no other operation than data hold is performed, and to wake up the micro-computer into operation for a short time for performing its jobs, such as heater control, sampling, and data processing. Since a micro-computer for operating a metal oxide semi-conductor gas sensor has not heavy jobs and can process at a low speed, the micro-computer may be operated with a duty ratio of one tenth, for example, and its power consumption can be reduced to one tenth of the power in continuous operation. Similarly, the buzzer and the LED are operated intermittently, when alarming, to reduce their power consumption.

BEST EMBODIMENT

Figure 1:
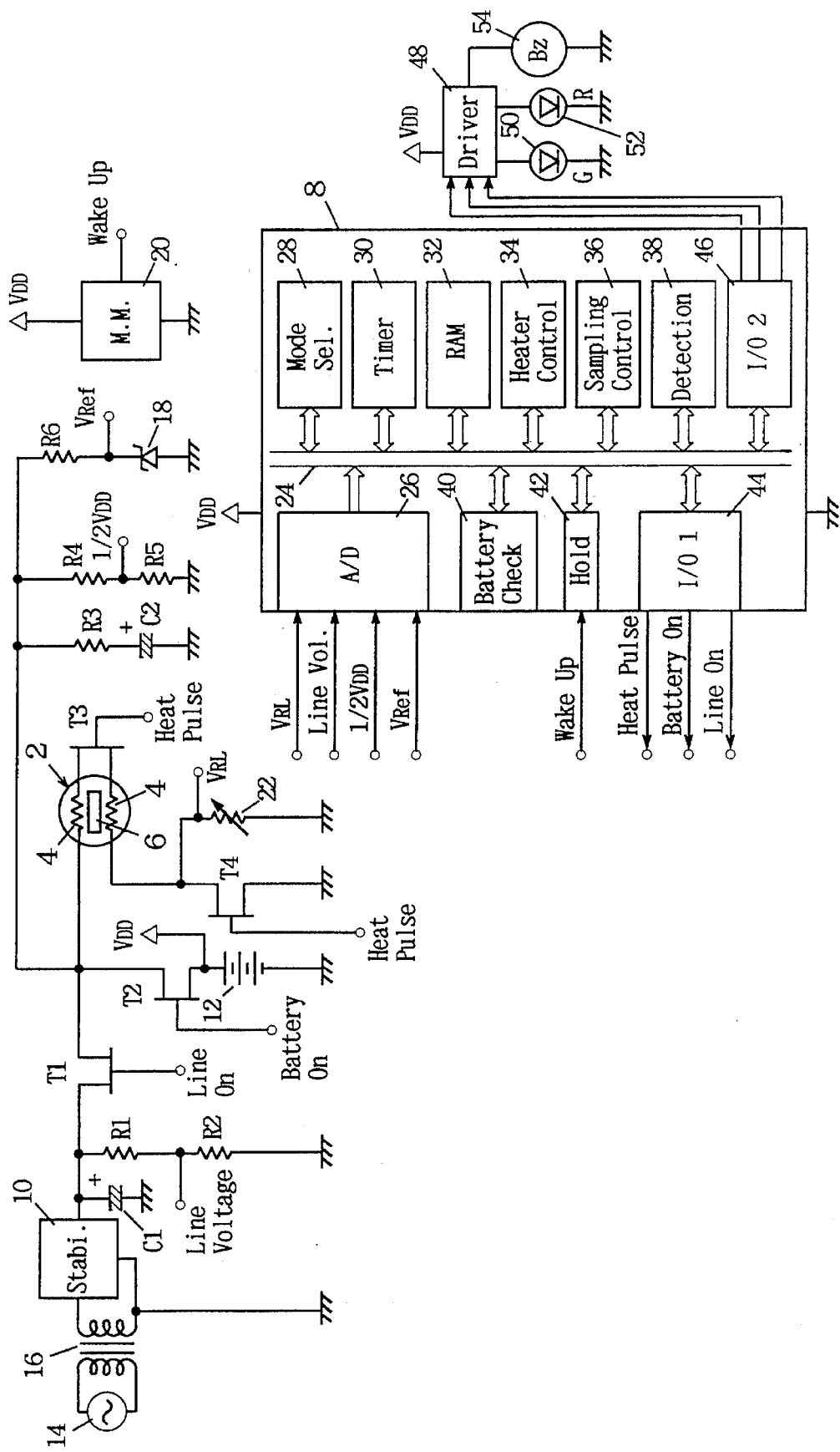
FIG. 1 is a block diagram of the CO detector according to the embodiment.
Figure 15:
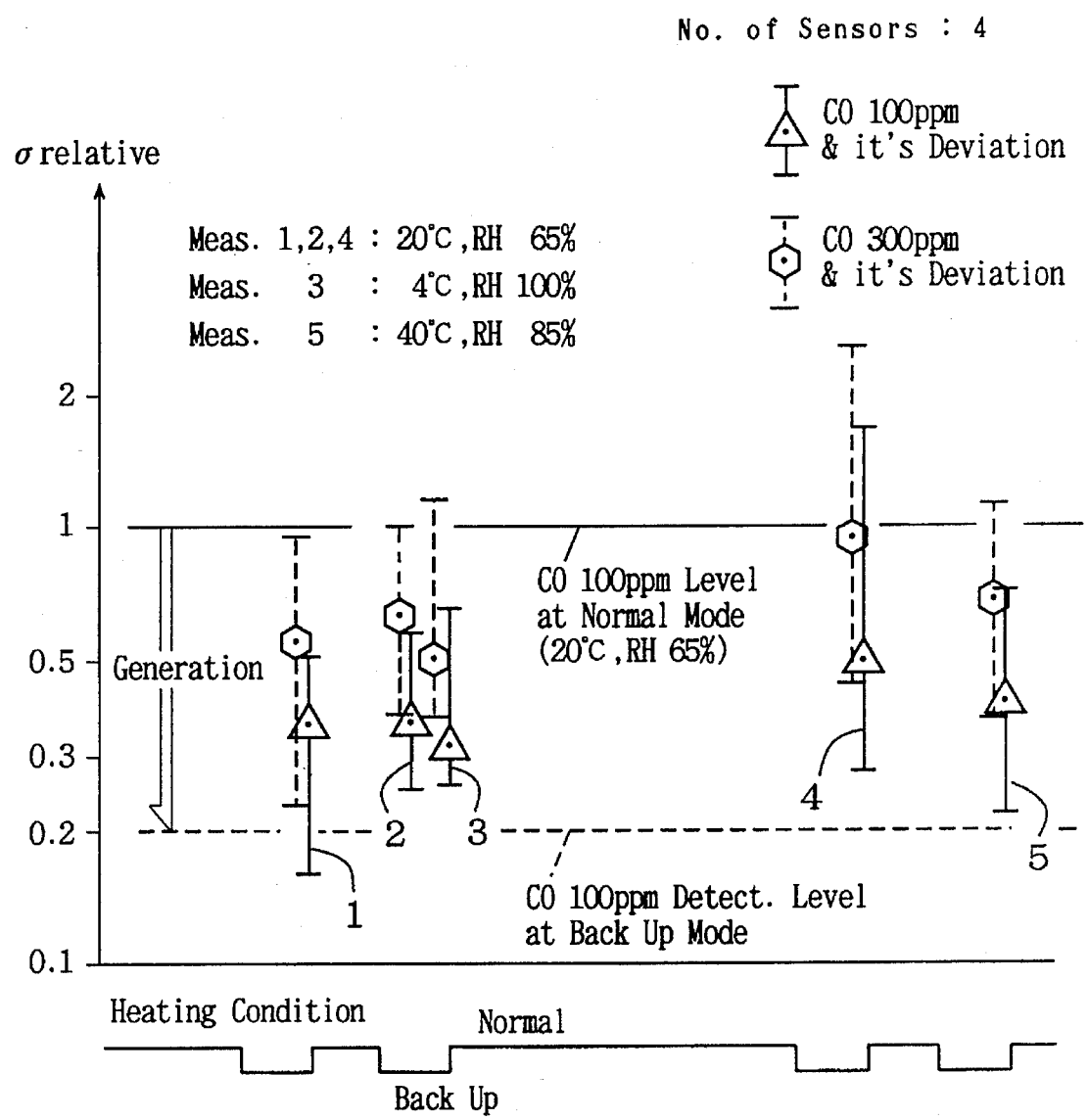
FIG. 15 is a characteristic diagram showing the dependency of the outputs for both 100 ppm CO and 300 ppm CO on temperature and on humidity.
Figure 16:
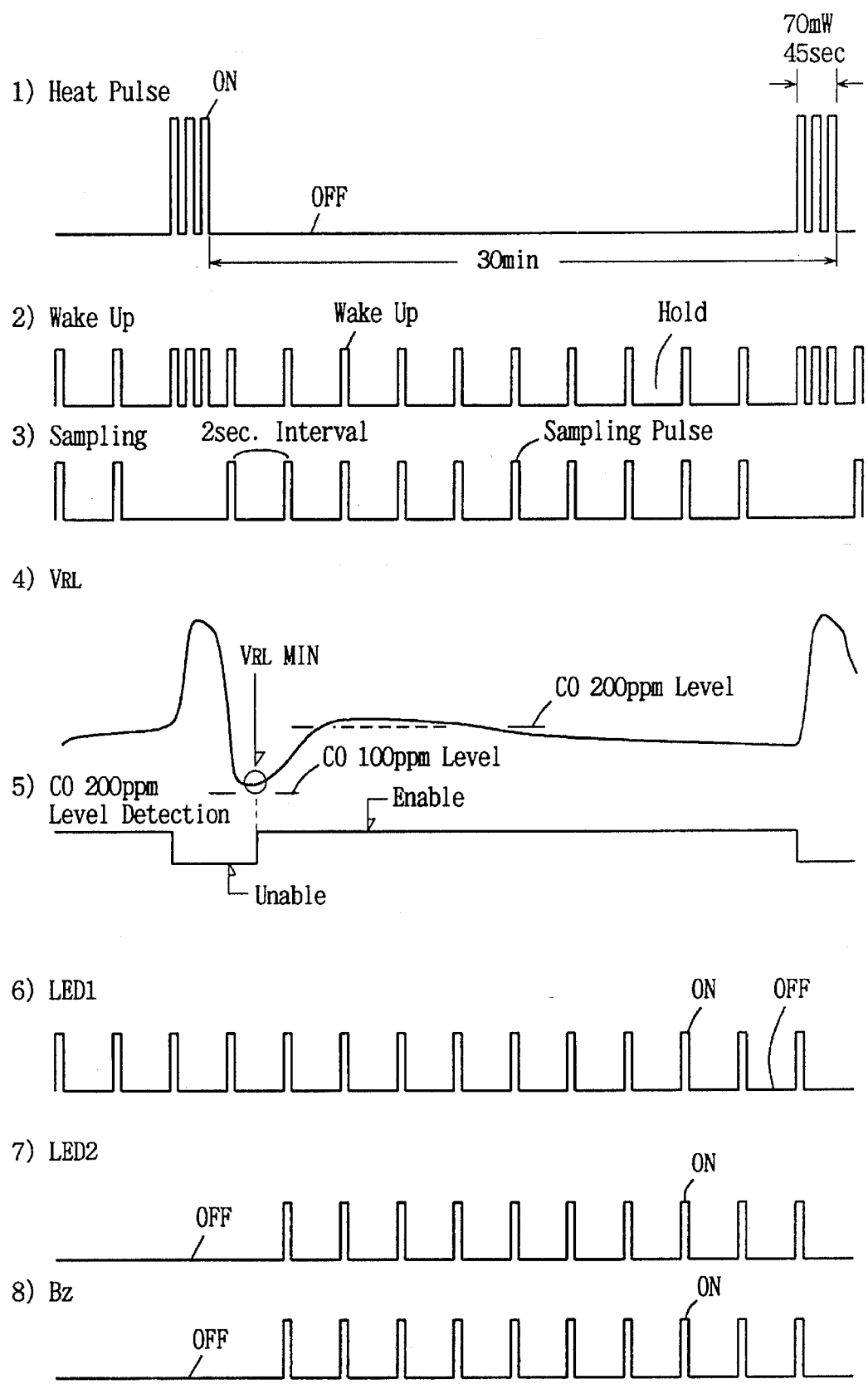
FIG. 16 is a waveform diagram in the backup mode.

FIGS. 1–16 show the embodiment. FIG. 1 shows the block circuit of the CO detector; FIGS. 2–7 show its operational flow; FIGS. 8–14 show the sensor responses to gases in the backup operation; FIG. 15 shows the ambient temperature and humidity dependence of the sensor output; and FIG. 16 shows waveforms of various parts in the detector.

As shown in FIG. 1, the detector includes a metal oxide semi-conductor gas sensor 2 which comprises two heaters 4, 4 and a metal oxide semi-conductor 6 whose resistance decreases in contact with CO. The sensor 2 is, for example, TGS 203 which is commercially produced and available through Figaro Engineering Inc. The heaters 4 and 4 which also serve as electrodes are embedded into SnO2 semi-conductor 6, and an active charcoal filter is provided for removing Nox and organic solvent vapors such as ethanol vapor. Other metal oxide semi-conductors such as In2O3 or ZnO are also usable and the configuration of the heaters 4 and 4 is arbitrary.

The detector is equipped with a micro-computer 8 which is, for example, a one chip micro-computer, with RAM, input output devices, an AD-converter, and ROM which is not shown in the figure. The micro-computer 8 operates in an operation mode and sleeps in a hold mode without any operation but holding the relevant data. Denoted at 10 is a power supply such as a constant voltage power supply with an output of 5 V, and 12 is a backup battery with a 6 V output comprising, for example, 4 alkaline dry cells in series. 14 is a transformer for reducing the output of a commercial power supply 16 into the input power to the power supply 10. Denoted at 18 is a zener diode for producing a reference voltage VREF, and 20 is a multivibrator for changing the mode of the micro-computer 8 between the operational mode and the hold mode. 22 is a variable resister for setting an alarm level at 100 ppm CO in a normal mode. T1–T4 are switches such as FETs, R1–R6 are resisters, and C1 and C2 a re capacitors for reducing ripples.

The micro-computer 8 has a bus 24 and a four channel AD-converter 26 with the standard voltage VREF supplied by the zener diode 18. The computer 8 further includes a mode selector 28 for storing a flag indicating whether the detector is in a normal mode or in a backup mode and for storing operational parameters depending upon the modes. The computer 8 is further equipped with a timer 30, RAM 32, a heater controller 34, a sampling controller 36, a detection unit 38, a battery checker 40, a hold controller 42, and input output device 44 and 46. The I/O 44 controls the switches T1–T4 for controlling the heaters 4 and 4 and for sampling sensor output VRL across the variable resister 22. Denoted at 48 is a driver for driving a green LED 50, a red LED 52, and a piezo buzzer 54 according to the signals of the I/O 46. The green LED 50 indicates the operation of the detector, and the red LED 52 and the buzzer 54 are both for alarm.

The gas sensor 2 is usually operated under the normal mode. In the normal mode, the TGS 203 sensor 2 is operated under its standard operational condition for 60 seconds at the higher temperature (maximum temperature of about 300° C.) and for 90 seconds at the lower temperature (minimum temperature of about 80° C.), and its output just before the termination of the lower temperature period is sampled through the output VRL across the variable resister 22. The sensor 2 is operated in a 150 second cycle, and the sampling is done in a 150 second interval.

If power cut or trouble of the power supply 10 makes the output across the resister R2 drop, the AD-converter 26 will detect it and change the operational mode into the backup one. In the backup mode, the switch T1 is off and the detector runs with the power of the battery 12 supplied through the switch T2.

The Table 1 tabulates the operational conditions for both the normal mode and the backup mode.

TABLE 1

The Operational Conditions of the Detector

|  | Normal Mode | | Backup Mode | |
| --- | --- | --- | --- | --- |
|  | Power | Condition | Power | Condition |
| Gas Sensor (TGS 203) |  | Pulse Drive |  | Pulse Drive |
| Decrease in |  |  | Compensated with Pulse |  |
| Battery Output |  |  | Width Modification |  |
| Operating Cycle | 150 secs. |  | about 30 mins. |  |
| the higher temp. | 60 secs. × 700 mW, | 300° C. | 45 secs. × 70 mW | |
| the lower temp. | 90 secs. × 70 mW, | 80° C. | 30 mins. | Non-Heated |
| Average Power | 320 mW |  | 1.8 mW | |

TABLE 1-continued

| | The Operational Conditions of the Detector | | | |
|---|---|---|---|---|
| | Normal Mode | | Backup Mode | |
| | Power | Condition | Power | Condition |
| Micro-computer | 20 mW | | 1 mW | |
| | | | Operating Duty 1/20 | |
| LED1 (Green | 10 mW | Continuous | 1 mW | Blinking |
| Miscellaneous | 50 mW | | 1 mW | |
| Total Power | 400 mW | | 5 mW | |
| (Non-Alarm) | | | | |
| For Alarm | | | | |
| Piezo Buzzer | 15 mw | Continuous | 1.5 mW | (Operated |
| | | | for 1 sec./10 sec.) | |
| LED2 (Red) | 10 mW | Continuous | 1 mW | Blinking |
| Backup Time | | | Above 1 week | |

Figure 2:
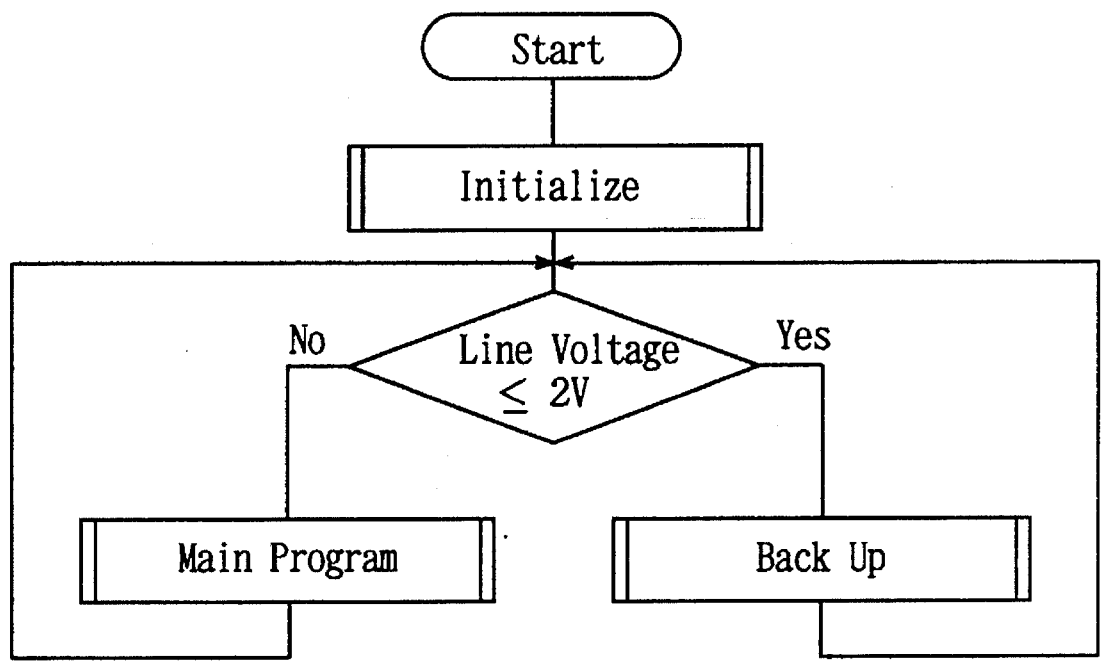
FIG. 2 is a flow chart showing mode changes between the normal mode and the backup mode.

The operation of the detector is described with reference to the flow charts in FIGS. 2–7. As shown in FIG. 2, the micro-computer 8 watches the power supply 10 through the output across the resister R2, and if the output decreases below 2 V, the computer 8 will turn off the power supply 10 and turn on the battery 12 through the switches T1 and T2. In the normal mode, the switch T1 is on, and the switch T2 is off.

Figure 3:
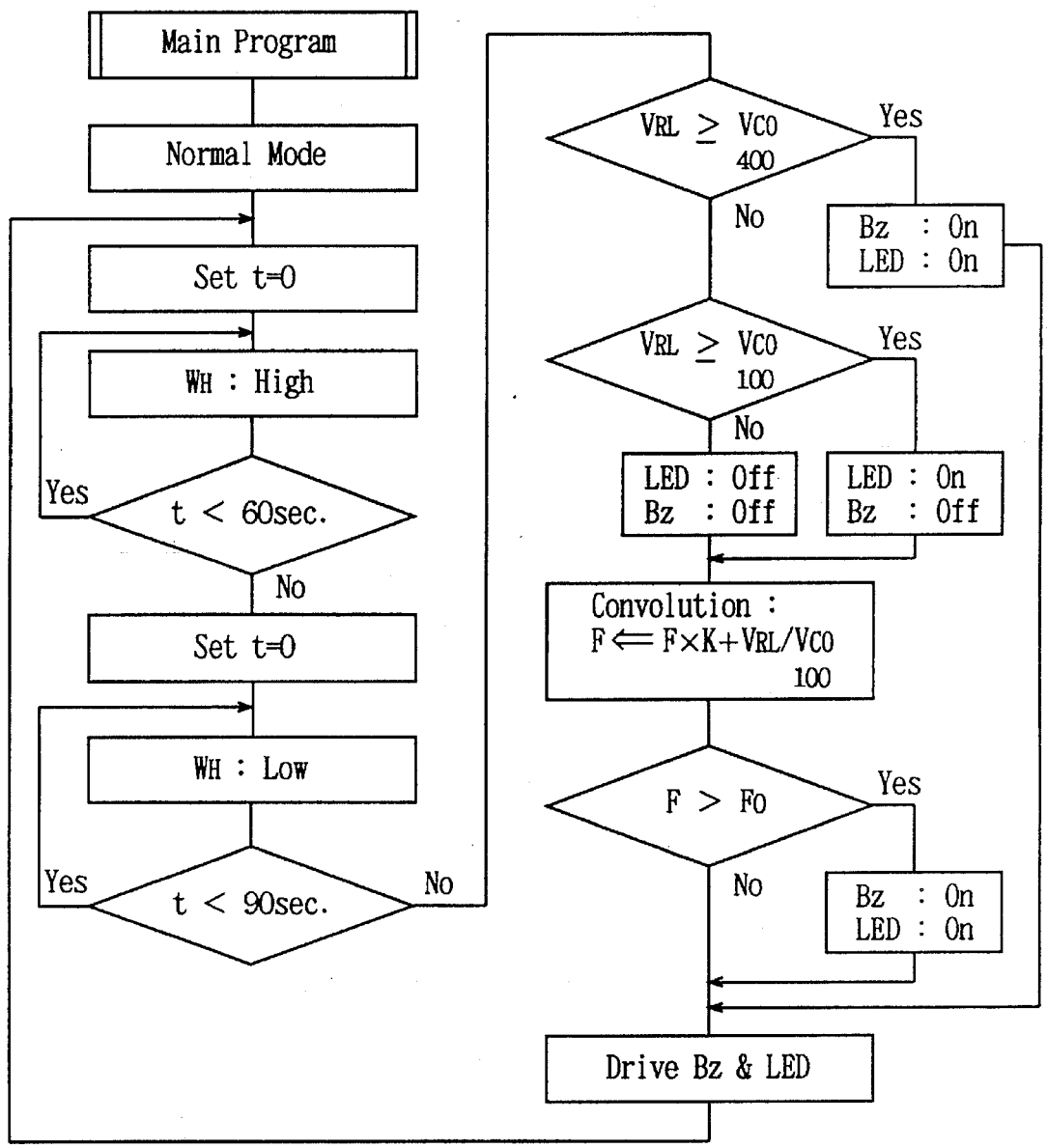
FIG. 3 is a flow chart showing operation in the normal mode.

In the normal mode, the voltage for each heater 4 and 4 is 0.8 V respectively at the higher temperature period with a sum of 1.6 V, and 0.25 V, respectively at the lower temperature period with a sum of 0.5 V, in addition the micro-computer 8 is operated at 5 V. To use a simple power supply 10 and to eliminate a power loss with reducing the 5, output of the power supply 10 into 1.6 V or 0.5 V, the switch T1 is turned on with the duty ratios at which the power consumptions are the same to those of 1.6 V and 0.5 V continuous drive. The duty ratio for the higher temperature period is about 12% and for the lower temperature period is about 1%. When heating the heaters 4 and 4, the switches T3 and T4 are turned on. When sampling the sensor output, switches T3 and T4 are turned off, and the output VRL across the variable resister 22 is inputted into the AD-converter 26. As shown in FIG. 3, the detection unit 38 sums up the sensor output according to the following formula for translating it into the CO hemoglobin concentration in the blood F, where K is a constant less than 1, FNEW is a new CO hemoglobin concentration, FOLD is an old CO hemoglobin concentration 1 cycle before, VRL is the sensor output across the resister 22, and VCO100 is a sensor output in 100 ppm CO.

$$FNEW = FOLD \times K + VRL/VCO100 \quad (1)$$

The detection unit 38 provides three kinds of alarms: presence of CO whose concentration is more than 400 ppm, presence of CO whose concentration is between 100 and 400 ppm, and presence of CO hemoglobin whose concentration exceeds its allowable range. If CO concentration is more than 400 ppm or CO hemoglobin concentration is above its allowable range, the LED 52 and the buzzer 54 will be operated continuously, while when CO concentration is between 100 and 400 ppm, just LED 52 will be lit continuously. If CO hemoglobin concentration exceeds the allowable range, while CO concentration is between 100 and 400 ppm, the LED 52 and the buzzer 54 will be operated continuously. When CO concentration is below 100 ppm and CO hemoglobin concentration is within the allowable range, just the green LED 50 will be operated continuously to indicate that the detector is working.

Figure 4:
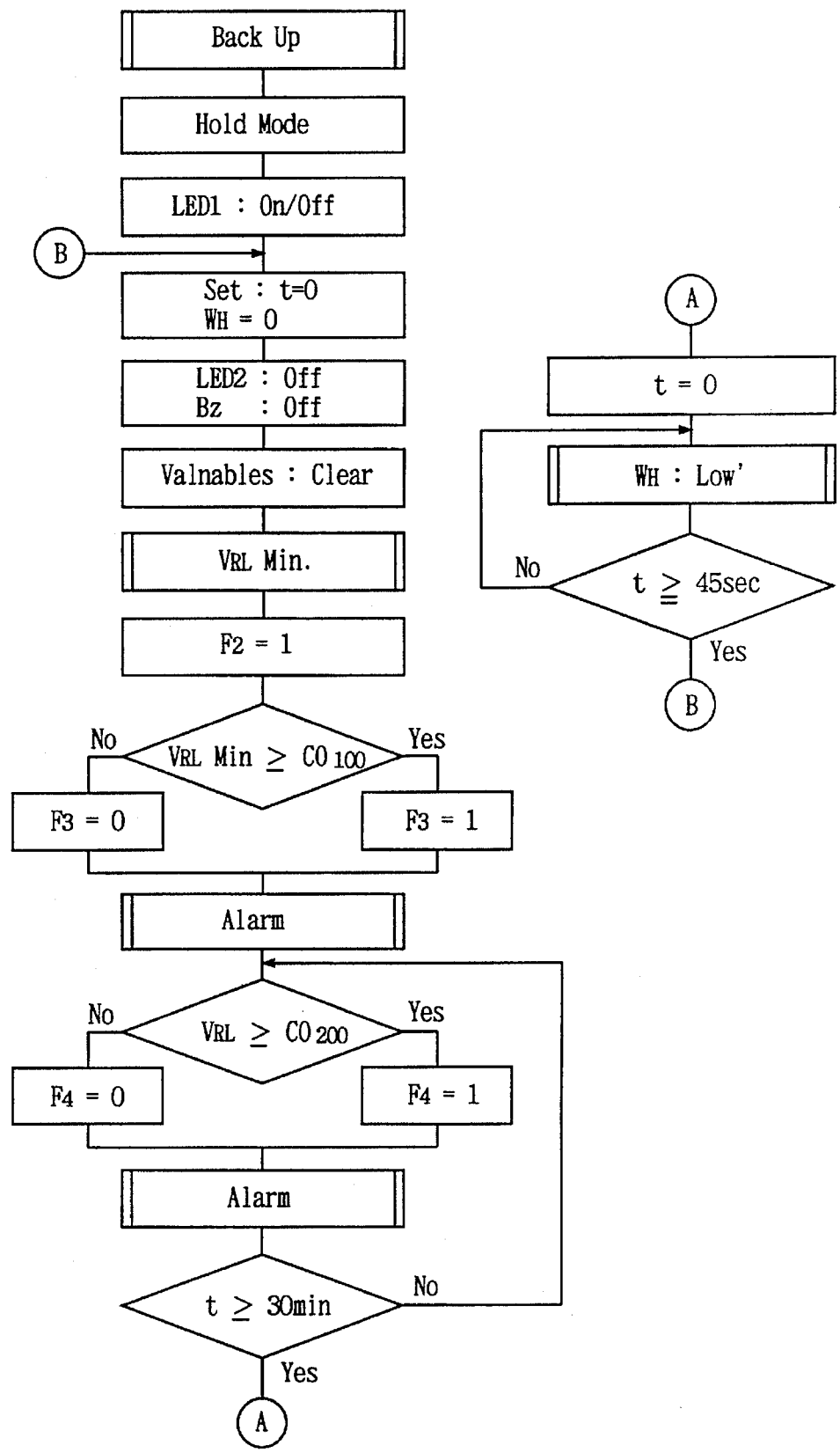
FIG. 4 is a flow chart showing operation in the backup mode.
Figure 5:
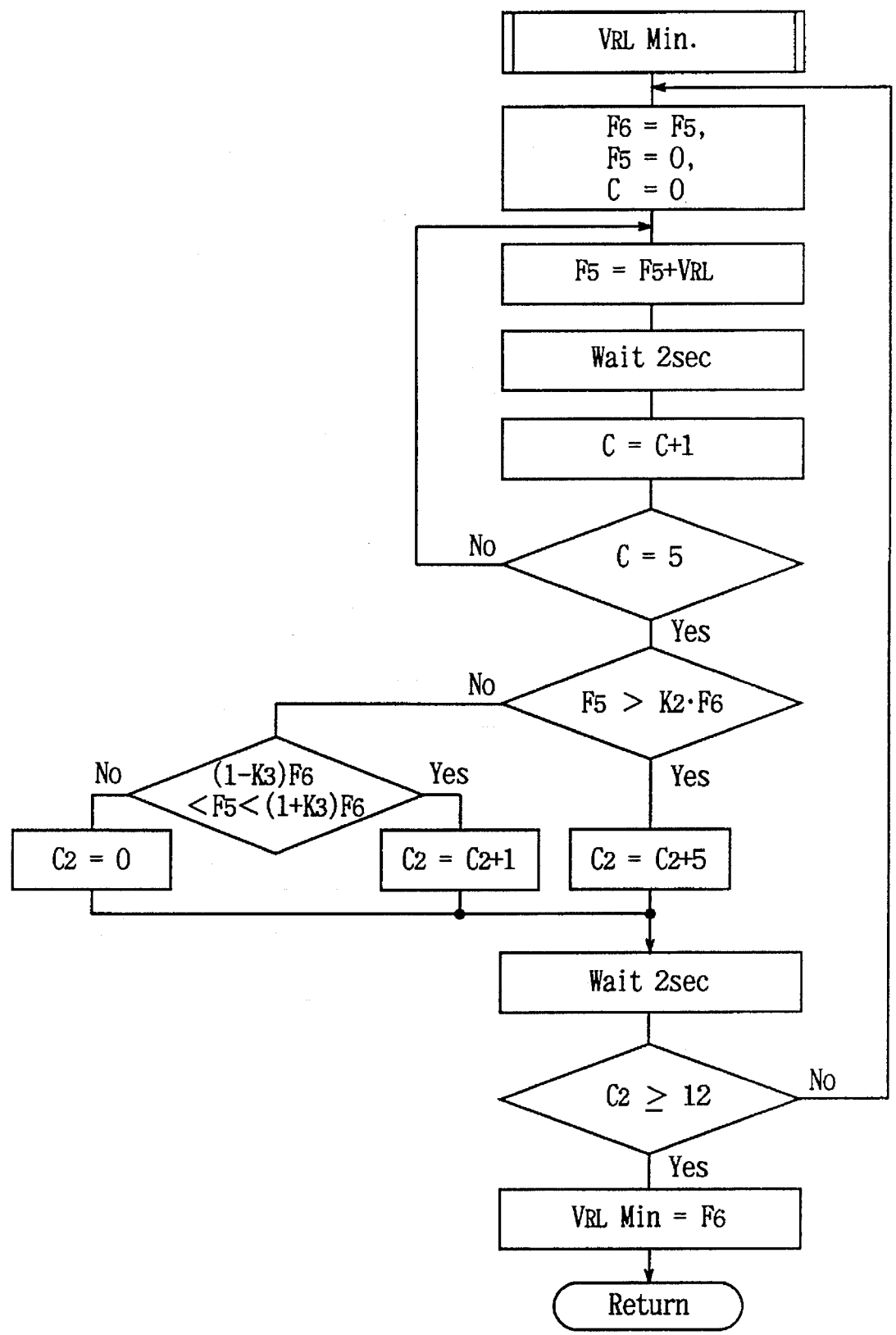
FIG. 5 is a flow chart showing the sampling of minimum sensor output.
Figure 6:
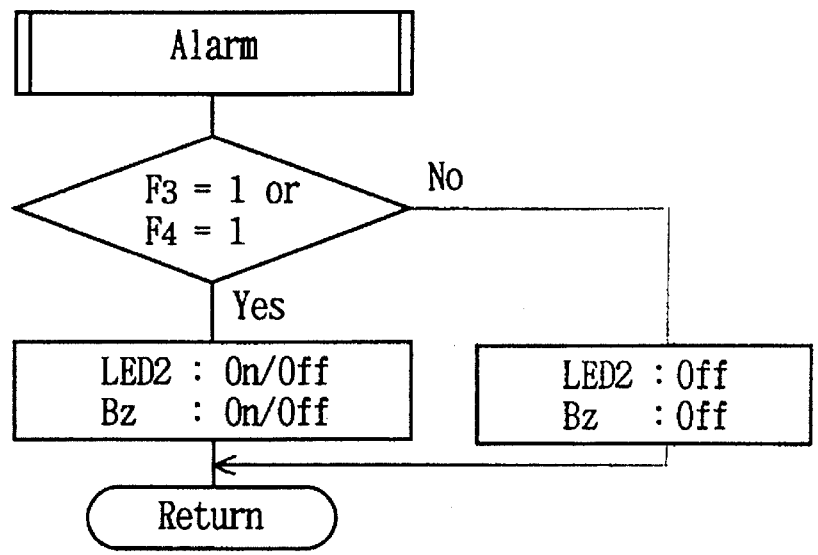
FIG. 6 is a flow chart showing alarm operation in the backup mode.
Figure 7:
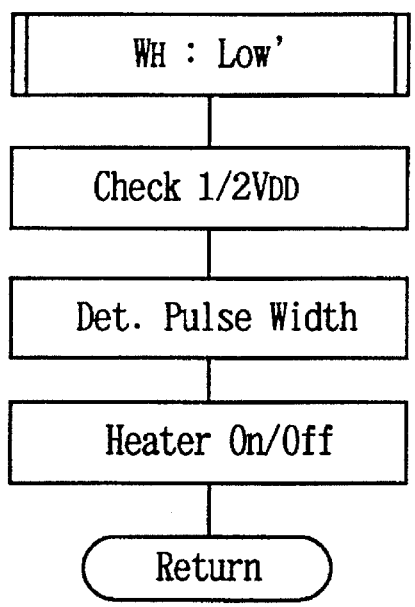
FIG. 7 is a flow chart showing the heater control in the back up mode.

FIGS. 4–7 show the operation in the backup mode. FIG. 4 shows its main routine; and FIGS. 5–7 show each subroutine. When the AD-converter 26 detects that the voltage across the resister R2 becomes less than 2 V, it will set a flag in the mode selector 28, turn off the switch T1, and change the made into the backup mode. In that mode, the micro-computer 8 will be waken up into the operation mode by a timer output of the multivibrator 20 and after ending its jobs it will return into the hold mode. Since in the hold mode, the micro-computer 8 does no other jobs than maintaining the data stored, power consumption in the mode is negligible. The micro-computer 8 is in the operation mode with a duty ratio of about 1/20, because the operation of the gas sensor 2 and relevant data processing require just light duty, therefore its effective power consumption is reduced to about 1 mW from 20 mW at continuous operation. The green LED 50 is turned on for one second per 10 seconds, for example, with a power consumption of 1 mW, to indicate power cut trouble.

In the backup mode, the operation cycle of the timer 30 is changed to 30 minutes 45 seconds, at the beginning of each cycle the relevant variables are cleared to zero, and the buzzer 54 and the LED 52 are switched off, if they have been turned on. Subsequently the sensor output VRL is sampled with 2 second intervals, at the timing when the switch T2 is turned on and the switches T3 and T4 are turned off.

For the final 45 seconds in the cycle, the switches T2, T3, and T4 are intermittently turned on for heating the sensor pulsively. The power consumption for the pulse heating period (45 seconds) is, for example, 70 mW, and it corresponds to heating each heater 4 and 4 with 0.25 V continuously. For eliminating power loss with lowering the 6 V output of the battery 12 into 0.5 V, the heating pulse for 45 seconds is divided into plural sub-pulses of wave numbers of 100 Hz and pulse width of 0.1 msec, for example, and the duty ratio of the sub-pulse heating is 1/100.

By the way, the switch T2 is turned off except for the sampling et me and the sub-pulse heating time so that the power loss due to a current flowing in the semi-conductor 6 may be avoided. The resistance of the semi-conductor 6 may decrease as little as to 10 kΩ in CO contaminated air, and in that case the current flowing the semi-conductor 6 requires 2.5 mW, providing that the variable resister 22 is 4 kΩ.

As shown in FIG. 7, for watching the exhaustion of the battery 12, the AD-converter 26 reads the standard voltage VREF across the zener diode 18 and an output voltage ½ VDD across the resister R5, and the heater controller 34 compares them. When the output voltage ½ VDD decreases, the sub-pulse width will be increased so that the heater power for the pulse heating is kept constant. While not shown in the figure, the output voltage ½ VDD is simultaneously read by the AD-converter 26 when VRL is read, and the detection unit 38 divides the sensor output VRL by ½ VDD for compensating the decrease in the battery output.

In the backup mode, the semi-conductor 6 is heated for 45 seconds pulsively at about 30 minute intervals and is kept at room temperature except for the pulse heating period. The total power consumption of the detector is about 5 mW, since the gas sensor 2 requires 1.8 mW, the micro-computer 8 requires 1 mW, the LED 50 requires 1 mW, and miscellaneous parts of the detector require about 1 mW. Consequently, the battery 12 may support the detector over one week for example. The maximum temperature of the semi-conductor 6 appears just after the termination of the pulse heating period and is, for example, about 40°–50° C. plus room temperature. The power consumption of the sensor 2 is so reduced that it becomes smaller than that of the other circuit, and it is not so helpful to further reduce the sensor power. The maximum temperature for the pulse heating period is, for example, between room temperature plus 30°–150° C., preferably between room temperature plus 40°–100° C., and most preferably between room temperature plus 40°–80° C. The pulse heating period is, for example, from 5 seconds to 2 minutes, preferably from 30 seconds to 90 seconds. The reliability of CO detection and the power consumption increase with the pulse heating period and the maximum heating temperature, and the above range for the pulse heating period and the temperature are empirically determined by considering these two factors. The detection interval increases with the room temperature period, while the power consumption increases with decreasing the room temperature period, and the inventor has found the room temperature period is, for example, from 5 minutes to 2 hours and preferably from 15 minutes to 45 minutes.

After the pulse heating, the minimum of the sensor output VRL is sampled, while if it cannot be sampled, a stationary value of the sensor output after the pulse heating is sampled. A sampling algorithm is shown in FIG. 5. Providing that F5 is the summing up of the sensor output VRL five times and that F6 is an old value of F5, if $$F5 > K2 \cdot F6 \quad (K2 > 1) \quad (2)$$

then a value C2 is incremented by five. If $$(1-K3) \cdot F6 < F5 < (1+K3) \cdot F6 \quad (3)$$

then the value C2 is incremented by one. The formula (2) is a sampling condition for the minimum sensor output, and the formula (3) is a sampling condition for the stationary value. Here K3 is positive but is near nearly to zero. Of course a simple sampling algorithm for the stationary value can be usable. For example, if no minimum value has been sampled within 2 minutes after the completion of the pulse heating, the sensor output at the time may be used as the stationary value. If the formula (2) or (3) is not satisfied, the value C2 will be initialized to zero, and if the value C2 is equal to or larger than 12, the value F6 will be sampled as the minimum or the stationary value.

CO is detected by means of the minimum or stationary value after the pulse heating and it is compared with a level corresponding to 100 ppm CO for alarming if it exceeds the level. The level is calculated from an alarm level for 100 ppm CO in the normal mode without setting up the level independently. Since the minimum or stationary value is sampled at 30 minute 45 second intervals, an alarm level to 200 ppm CO is prepared to detect any rapid generation of a high concentration of CO. Since the sensor output is relatively large both during the pulse heating period and till the occurrence of the minimum or the stationary value, the detection for CO above 200 ppm in concentration is enabled after the detection of the minimum or the stationary value. Subsequently, the detection whether CO concentration is higher than 200 ppm is repeated at 2 second intervals. However the detection of 200 ppm CO has a low accuracy, therefore, if the dead time of 200 ppm CO detection is short, for example, in the case that the room temperature period is shorter than 15 minutes, the 200 ppm CO detection is unnecessary, As shown in FIG. 6, when CO is detected, the red LED 52 and the piezo buzzer 54 will be operated intermittently, for example, for 1 second per 10 seconds, so that their power consumptions is reduced, while simultaneously indicating the detector being in the backup mode. Thus additional power consumption for the alarm is 1 mW for the LED 52 and 1.5 mW for the buzzer 54 with their sum of 2.5 mW.

Table 2 shows the specification of the backup mode, and FIGS. 8–14 show the responses of the sensor in the mode.

TABLE 2

The Specification of the CO Detector in the Backup Mode

| Detection | |
|---|---|
| 100 ppm CO: | Detection within 30 minutes |
| 200 ppm CO: | Detection is enabled after the sampling of the minimum or stationary sensor output |
| <20 ppm CO: | No detection |
| 1000 ppm H2: | No detection |
| 1000 ppm ethanol: | No detection |
| Parameters | |
| 100 ppm CO detecting level: | Calculated from the 100 ppm CO level in the normal mode |
| Sampling Condition: | The Minimum or stationary sensor output after the pulse heating |
| 200 ppm CO detecting level: | Calculated from the 100 ppm CO level in the normal mode |
| Sampling Condition: | Enabled after the sampling of the minimum or the stationary output with 2 seconds interval |

Figure 8:
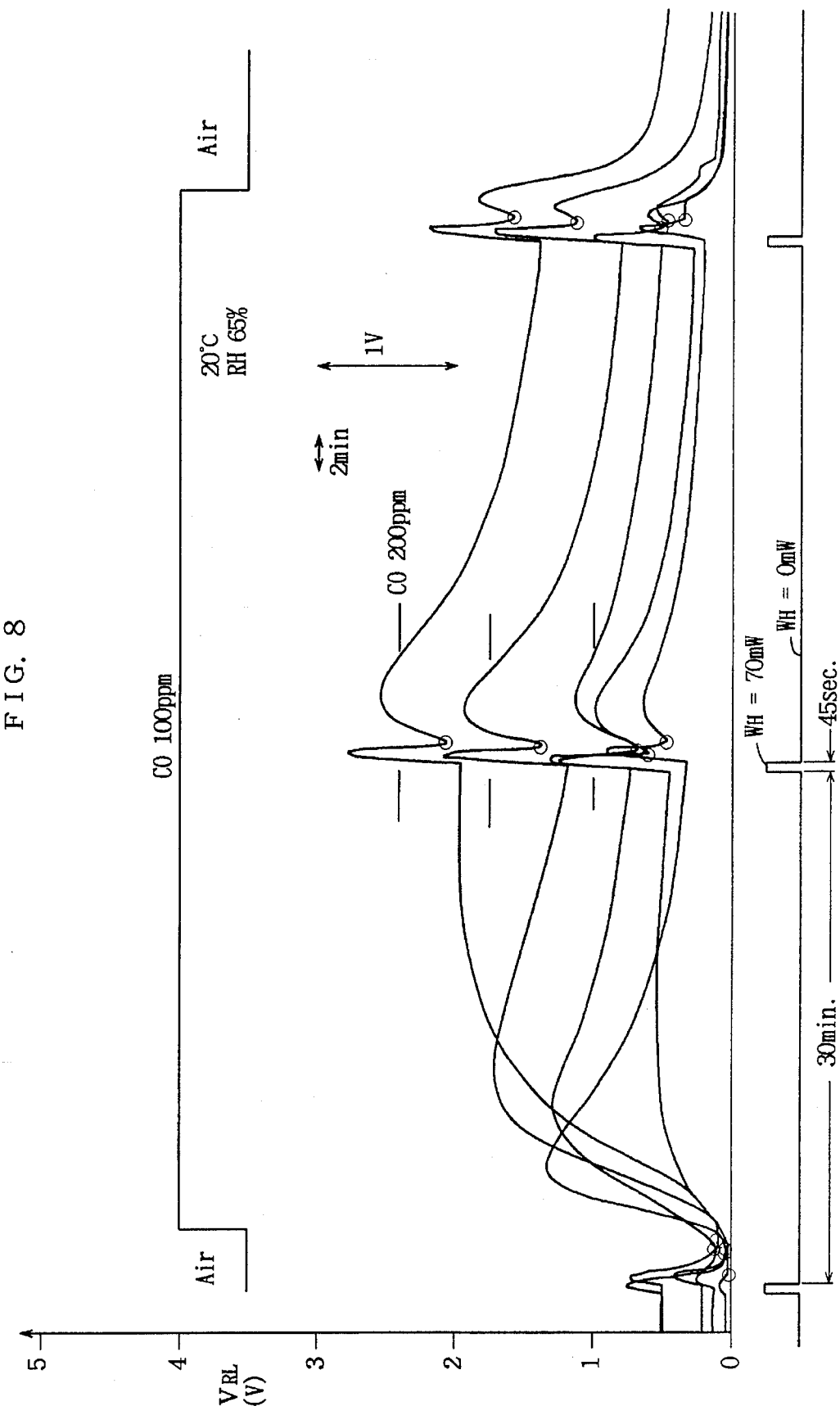
FIG. 8 is a characteristic diagram showing gas sensor outputs in CO 100 ppm containing air of 20° C. and relative humidity 65% in the backup mode.

FIG. 8 shows the responses of the five CO sensors (TGS 203) in a test box to 100 ppm CO at 20° C. at relative humidity 65%. The sensors had been operated in the backup mode for 24 hours before the measurement. The responses to CO were complex and some of them showed maxima, while the others not. However, both in air and in CO contaminated air, the minimum sensor outputs appeared after the pulse heating period.

Figure 9:
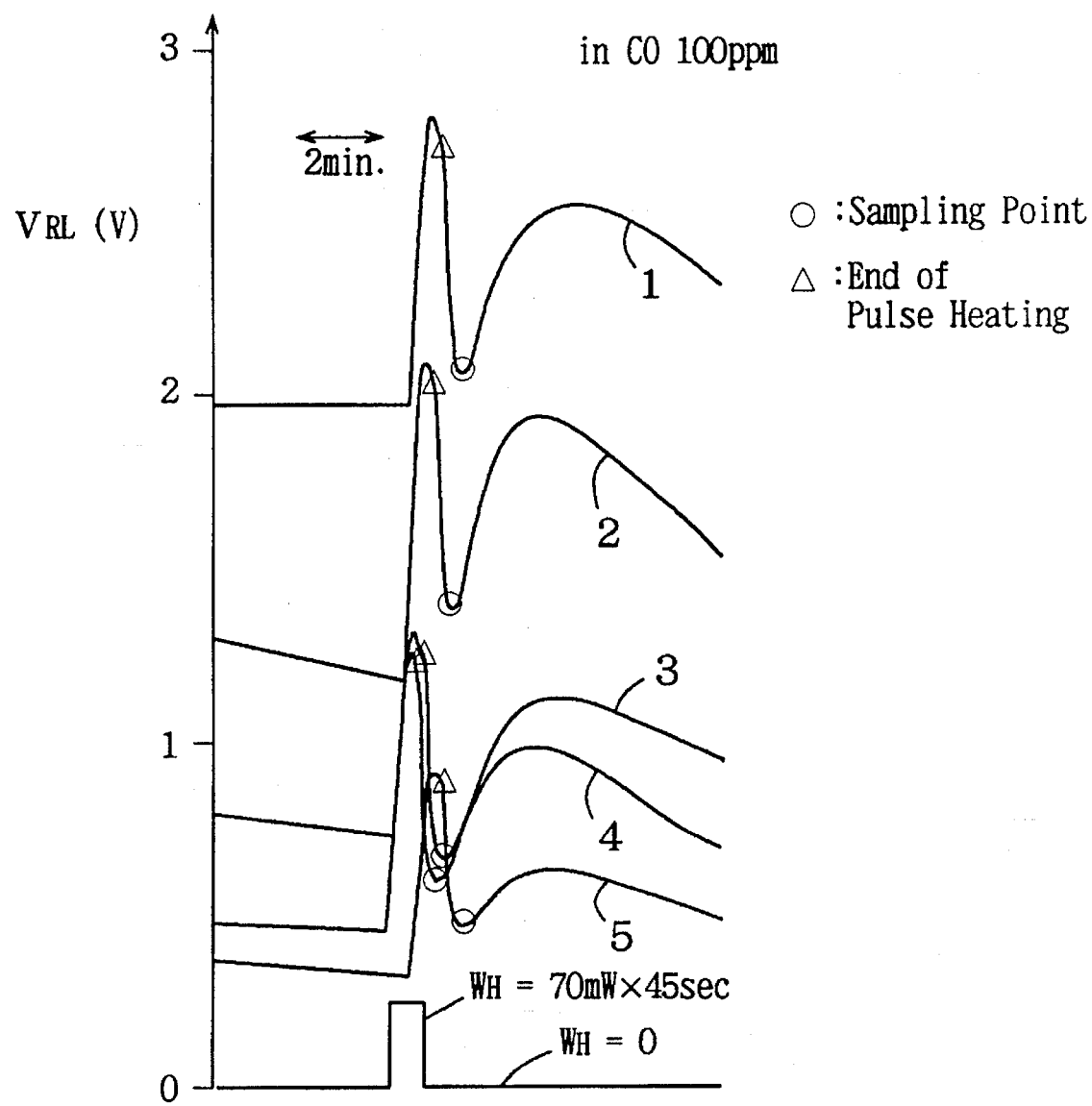
FIG. 9 is a characteristic diagram showing gas sensor responses to 100 ppm CO in the backup mode.
Figure 10:
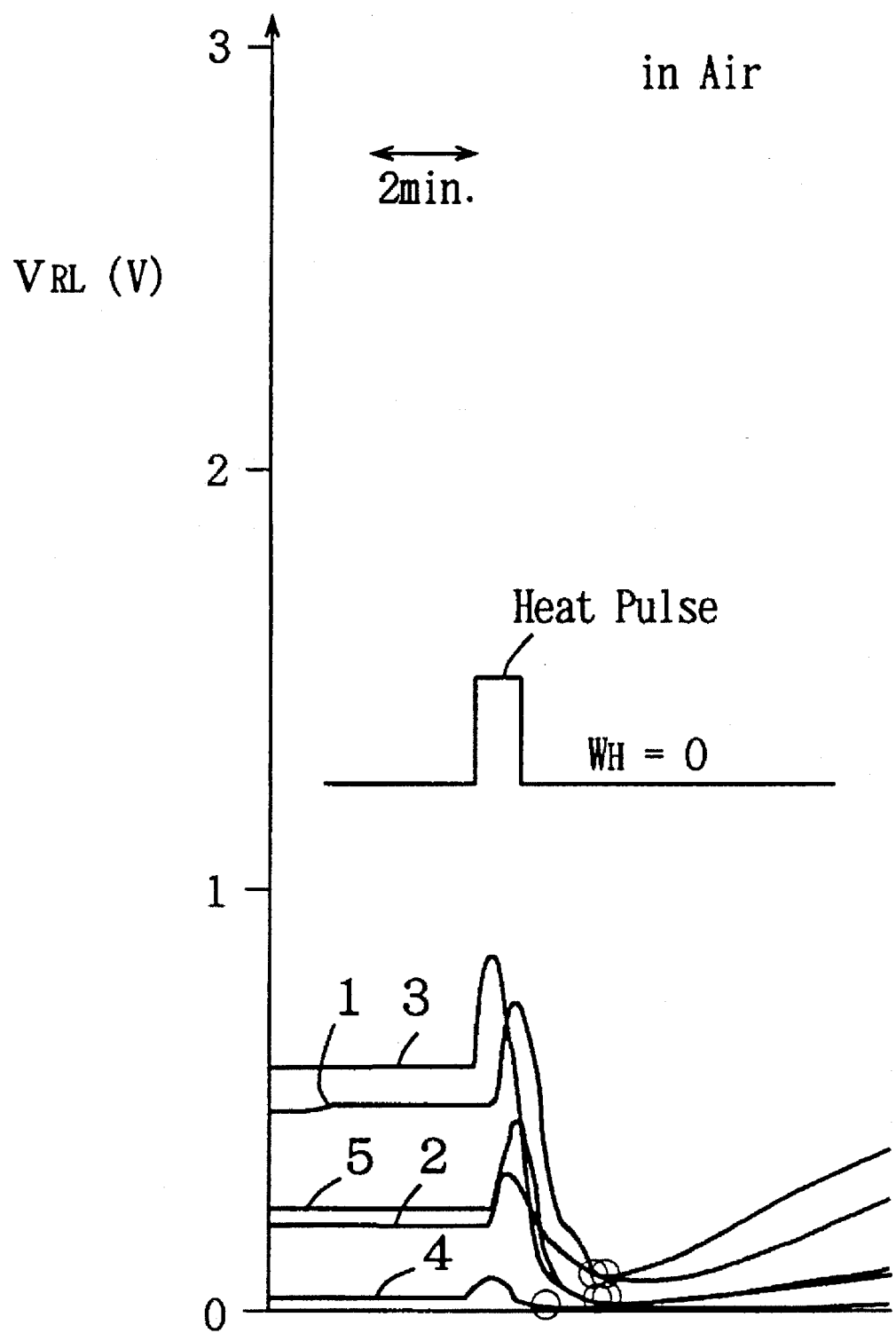
FIG. 10 is a characteristic diagram showing the responses to air in the backup mode.
Figure 11:
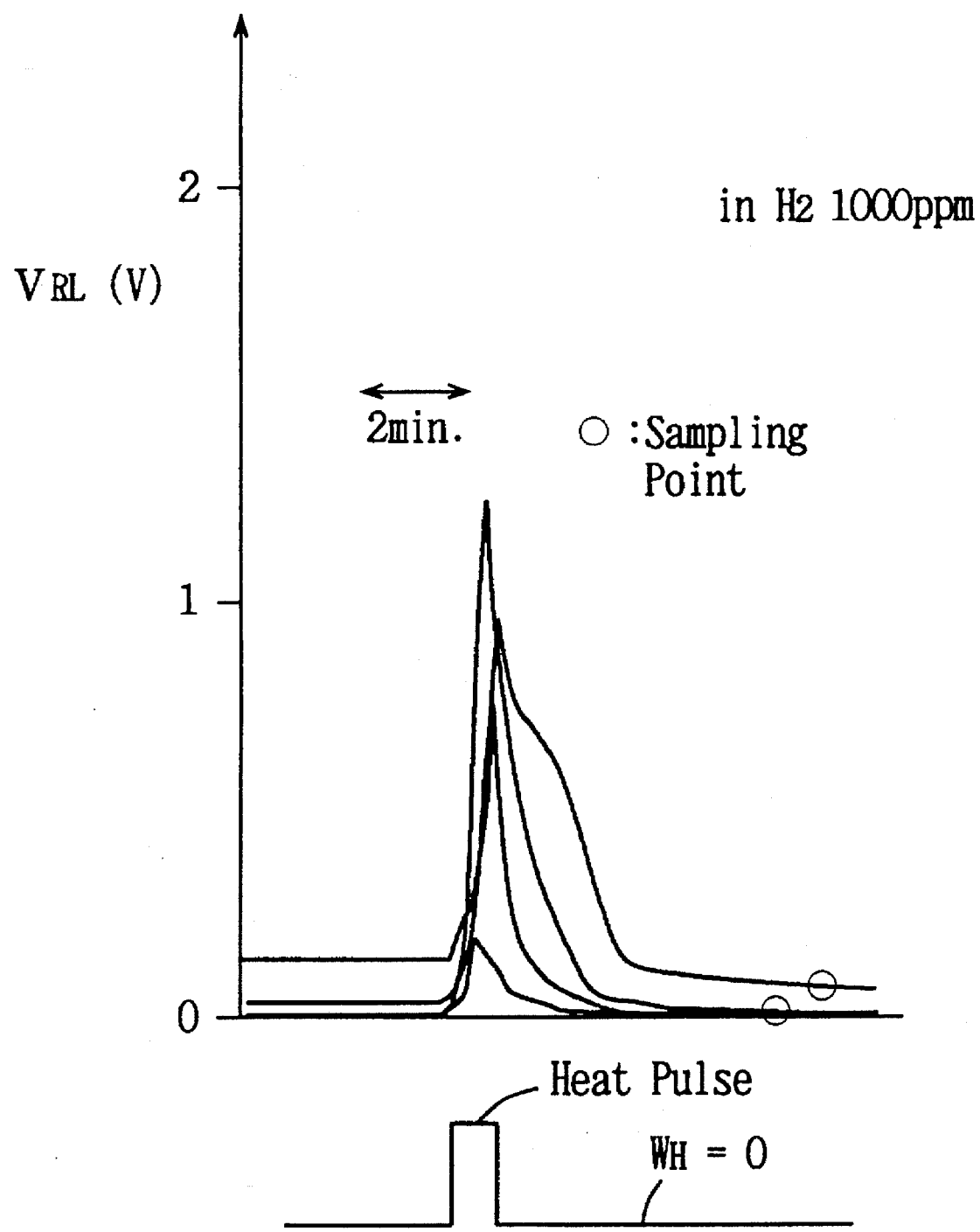
FIG. 11 is a characteristic diagram showing the responses to H2 1000 ppm containing air in the backup mode.
Figure 12:
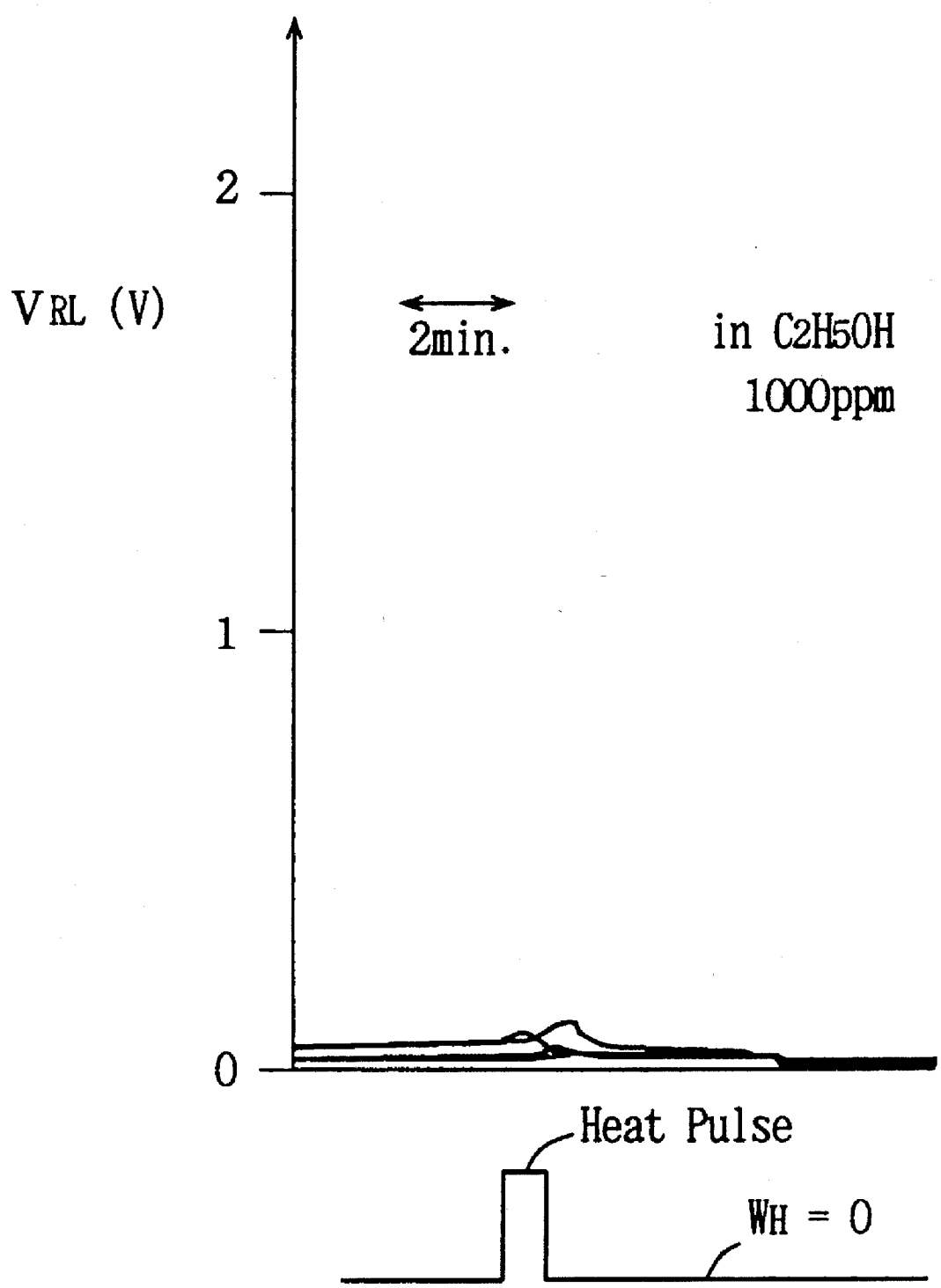
FIG. 12 is a characteristic diagram showing the responses to ethanol 1000 ppm containing air in the backup mode.

The minima correlate strongly to CO concentration. FIG. 9 shows the responses to 100 ppm CO after the pulse heating; FIG. 10 shows those to air; FIG. 11 shows those to 1000 ppm H2; and FIG. 12 shows those to 1000 ppm ethanol. As shown in FIG. 10, in air the minimum sensor outputs after the pulse heating are small. As shown in FIG. 11, in H2 the sensor outputs decrease monotonically to small stationary values after the pulse heating without affording a minimum sensor output, and as shown in FIG. 12, the sensor outputs in ethanol are small at any times. In contrast to them, in CO the minimum sensor outputs after the pulse heating are relatively large. The sensor output during the pulse heating is large both in air and in H2 containing air and it is not adequate for CO detection. Further, the sensor output just before the pulse heating is sometimes large even in air, and it weakly suggests the presence of CO.

Figure 13:
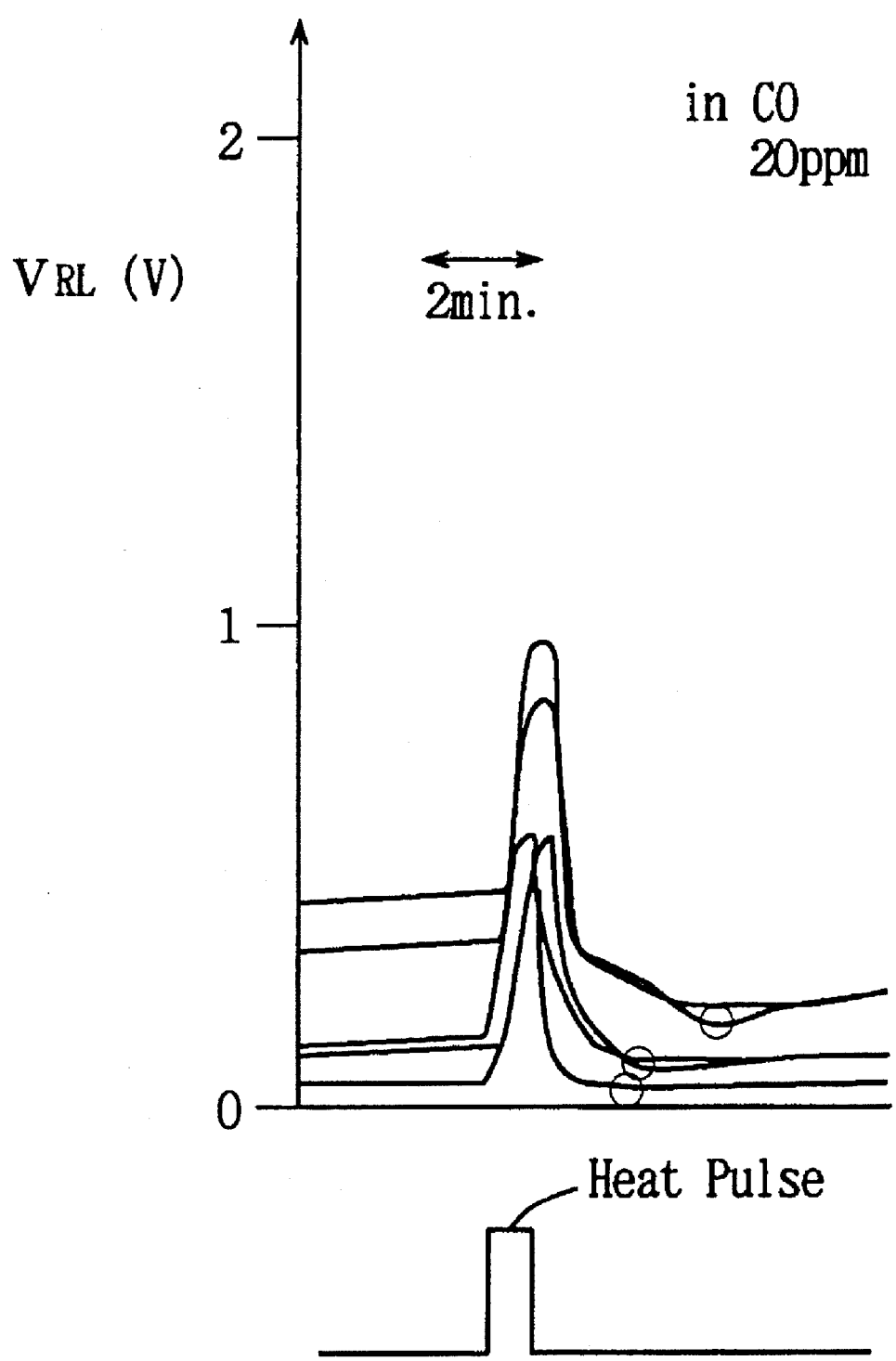
FIG. 13 is a characterisic diagram showing the responses to 20 ppm CO in the backup mode.
Figure 14:
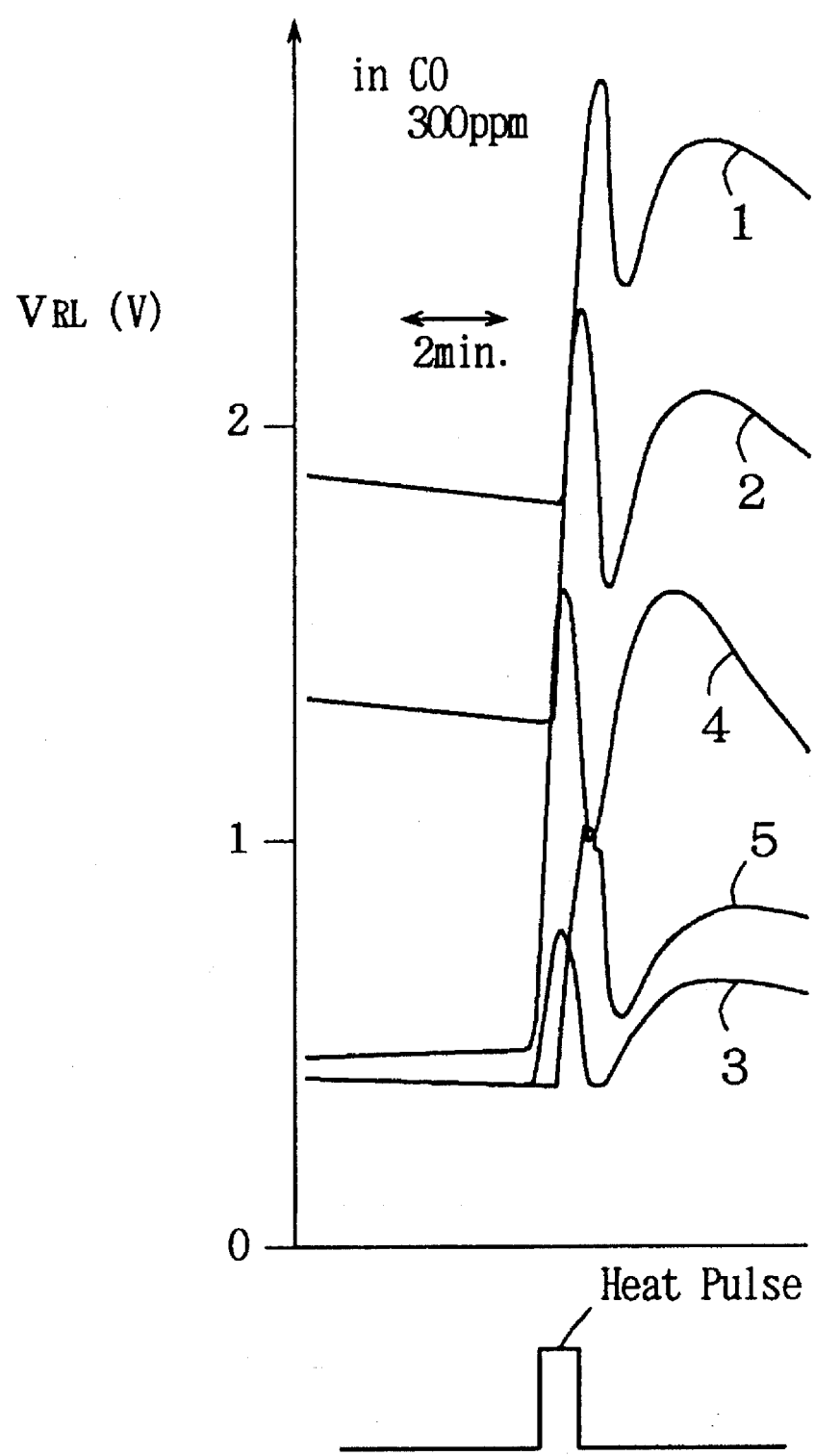
FIG. 14 is a characteristic diagram showing the responses to 300 ppm CO in the backup mode.

FIG. 13 shows sensor responses to 20 ppm CO, and FIG. 14 shows responses to 300 ppm CO. As shown in FIG. 13, minimum outputs in 20 ppm CO after the pulse heating are small, therefore 20 ppm CO can not be detected, and it is noteworthy that 20 ppm CO is not harmful and is within an allowable range. When responses to 300 ppm CO (FIG. 14) and those to 100 ppm CO (FIG.9) are compared with each other, the difference between them is small, so that quantitative detection of CO is difficult. Thus the detector according to the embodiment indicates whether CO of a concentration above an al lowable range is present or not and is little affected by H2 or ethanol.

As already known, at about room temperature, outputs of metal oxide semi-conductor gas sensors are strongly affected by humidity, and it is necessary to confirm the humidity dependence of the detection outputs being within an allowable range. FIG. 15 shows of outputs in 100 ppm CO and in 300 ppm CO at various ambient temperatures and humidities. The outputs are minimum sensor outputs after the pulse heating. The ordinate shows electric conductivity of the metal oxide semi-conductor 6 being normalized to one by the conductivity in the normal mode in 100 ppm CO. The specimens comprised four sensors which had been used in the normal mode, then they were kept in the backup mode for 24 hours, and their outputs were measured in 100 ppm CO and in 300 ppm CO at an atmosphere of room temperature of 20° C. and relative humidity of 65%. After the measurement, the sensors were kept in the normal mode for 24 hours, and subsequently they were operated under the backup mode, and their outputs were measured at an atmosphere of room temperature of 20° C. and relative humidity of 65%. Then, they were still operated under the backup mode for about 24 hours and their outputs were measured at an atmosphere of room temperature of 4° C. and relative humidity of 100%. Subsequently, the sensors were kept in the normal mode for five days, then they were operated under the backup mode for 24 hours, and their outputs at 20° C., relative humidity 65% were measured. After that, they were used for 24 hours in the normal mode, and the operational mode was changed to the backup mode. After 24 hours being kept in the backup mode, their outputs at 40° C., relative humidity 85% were measured. FIG. 15 shows random variations with the five measurements and dependence of the sensor outputs on various atmospheres comprising 20° C., relative humidity 65%, 4° C., 100%, and 40° C., 85%.

As shown in the figure, by setting the detection level to 100 ppm CO in the backup mode at 1/5 of the one to the same concentration of CO in the normal mode, almost every occurrence of CO 100 ppm can be detected. As already shown in FIG. 13, the output for 20 ppm CO is about one tenth of that for 100 ppm CO, so 20 ppm CO is hardly detected with setting the detection level as mentioned above.

FIG. 16 shows waveforms of various parts of the detector. The heating pulse onto the heaters 4 and 4 for 45 seconds are divided into plural sub-pulses, and the micro-computer 8 is in the hold mode except for the sub-pulse generation, sampling, and the operation of LED 50. Before these operations, the computer 8 is woken up by the multivibrator 20. Sampling is performed at 2 second intervals, and the minimum or stationary sensor output sampled is compared with the detection level for 100 ppm CO. Subsequently the detection for 200 ppm CO is enabled. Without occurrence of CO, the green LED 50 is blinked, and when occurrence of CO is detected, the red LED 52 will be blinked and the buzzer 54 will be intermittently operated.

While the embodiment has described specific operational condition detailedly, it is just an example, and the type of metal oxide semi-conductor 2 is arbitrary.

I claim:
1. A method for CO detection comprising:
a step for operating a metal oxide semi-conductor gas sensor which comprises at least a heater and a metal oxide semi-conductor whose resistance changes upon contact with CO, with a first power supply under a first heating cycle, so that the metal oxide semi-conductor is heated at a relatively high temperature suitable for purging said semi-conductor, and at a relatively low temperature suitable for CO adsorption on said semi-conductor,
a step for detecting CO by measuring the resistance of the metal oxide semi-conductor at said relatively low temperature,
a step for detecting power cut of the first power supply and for outputting a power cut signal,
a step for connecting a backup battery to the gas sensor in place of the first power supply, based upon the power cut signal,
a step for operating the gas sensor under a second heating cycle repetitively upon the power cut signal so that the metal oxide semi-conductor is pulsively heated and is kept from being heated except for the pulse heating time,
a step for detecting CO by measuring the resistance of the metal oxide semi-conductor after the pulse heating in the second heating cycle, and
operating a micro-computer for controlling the heater and for detecting CO by measuring the resistance of the metal oxide semi-conductor under the second heating cycle in an operation mode both for controlling the heater and for detecting CO by measuring the resistance of the metal oxide semi-conductor, and also in a hold mode without operation alternately.

2. A method for CO detection as recited in claim 1, wherein the maximum heating temperature of the metal oxide semi-conductor during the second heating cycle is in the range of from ambient temperature plus 30° C. to ambient temperature plus 150° C.

3. A method for CO detection as recited in claim 1, wherein the pulse heating is performed for 5 seconds to 2 minutes and the gas sensor is kept from being heated for 5 minutes to 2 hours.

4. A method for CO detection as recited in claim 1, wherein the step for detecting CO under the second heating cycle includes sampling a maximum or stationary resistance of the metal oxide semi-conductor after the pulse heating.

5. A method for CO detection as recited in claim 4, wherein the step for detecting CO under the second heating cycle further includes a step for detecting CO by measuring the resistance of the metal oxide semi-conductor after the sampling of the maximum or the stationary resistance.

6. A method for CO detection in claim 1, wherein the backup battery is connected to the heater of the gas sensor intermittently during the pulse heating.

7. A method for CO detection as recited in claim 1, wherein an LED and a buzzer both for indicating the presence of CO are provided, and they are intermittently operated under the second heating cycle when the presence of CO is detected.

8. A method for CO detection as recited in claim 7, wherein the metal oxide semi-conductor is intermittently connected to the backup battery under the second heating cycle after the pulse heating for sampling its resistance.

9. A CO detector comprising;
a metal oxide semi-conductor gas sensor which includes a metal oxide semi-conductor whose resistance changes in contact with CO and at least a heater for heating the semi-conductor, a first power supply, and means for controlling the heater by inputting the output of the power supply to the heater so that the metal oxide semi-conductor is heated at a relatively high temperature and at a relatively low temperature alternately and periodically, a backup battery, means for detecting trouble of the first power supply, a switch for connecting either of the first power supply and the backup battery to the heater control means, a micro-computer both for controlling the heater control means and for sampling the resistance of the metal oxide semi-conductor for detecting CO, said micro-computer having at least two modes comprising an operational mode both for controlling the switch and the heater and for detecting CO by measuring the resistance of the metal oxide semi-conductor, and a data hold mode without operation but holding data stored in the micro-computer, and a timer, said micro-computer, when said trouble detecting means detects trouble of the first power supply, controlling both the switch and the heater control means so that the backup battery is connected to said heater control means and so that the metal oxide semi-conductor is heated pulsively and kept at ambient temperature alternately, and the micro-computer detecting CO by measuring the resistance of the metal oxide semi-conductor after the pulse heating, and said micro-computer undergoes the two modes alternately with the timer, when the trouble of the first power supply is detected.

10. A CO detector as recited in claim 9, wherein said micro-computer detects CO by determining the maximum or stationary resistance of the metal oxide semi-conductor after the pulse heating, when the trouble of the first power supply is detected.

11. A CO detector in claim 10, wherein said micro-computer generates a plurality of sub-pulses during the pulse heating for connecting the backup battery to the heater during the each sub-pulse, when the trouble of the first power supply is detected.

12. A CO detector in claim 9, wherein the detector as recited further comprises a buzzer and LED both for alarming the presence of CO, and the buzzer and the LED are intermittently operated, when CO is detected during the trouble of the first power supply.

13. A CO detector comprising:

a metal oxide semi-conductor gas sensor which includes a metal oxide semi-conductor whose resistance changes in contact with CO and at least a heater for heating the semi-conductor, a first power supply, and means for controlling the heater by inputting the output of the power supply to the heater so that the metal oxide semi-conductor is heated at a relatively high temperature and at a relatively low temperature alternately and periodically, a backup battery, means for detecting trouble of the first power supply, a switch for connecting either of the first power supply and the backup battery to the heater control means, and a controller having a timer and a micro-computer, said micro-computer controlling the heater control means and sampling the resistance of the metal oxide semi-conductor for detecting CO, said micro-computer having at least two modes comprising an operational mode both for controlling the switch and the heater and for detecting CO by measuring the resistance of the metal oxide semi-conductor, and a data hold mode without operation but holding data stored in the micro-computer, said micro-computer, when said trouble detecting means detects trouble of the first power supply, controlling both the switch and the heater control means so that the backup battery is connected to said heater control means and so that the metal oxide semi-conductor is heated pulsively and kept at ambient temperature alternately, and the micro-computer detecting CO by measuring the resistance of the metal oxide semi-conductor after the pulse heating, and said micro-computer undergoes the two modes alternately with the timer, when the trouble of the first power supply is detected.

* * * * *